United States Patent [19]

Koppe et al.

[11] 4,105,796

[45] Aug. 8, 1978

[54] PHARMACEUTICAL COMPOSITIONS CONTAINING RACEMIC OR OPTICALLY ACTIVE 1-(2,6-DIMETHYL-PHENOXY)-2-METHYLAMINO-PROPANE AND METHOD OF USE

[75] Inventors: Herbert Köppe; Werner Kummer; Helmut Stähle; Richard Reichl, all of Ingelheim am Rhein; Rolf Giesemann, Biberach an der Riss, all of Fed. Rep. of Germany

[73] Assignee: Boehringer Ingelheim GmbH, Ingelheim am Rhein, Fed. Rep. of Germany

[21] Appl. No.: 688,105

[22] Filed: May 19, 1976

[30] Foreign Application Priority Data

Jun. 2, 1975 [DE] Fed. Rep. of Germany ....... 2524363

[51] Int. Cl.$^2$ ........................................... A61K 31/135
[52] U.S. Cl. .................................................... 424/330
[58] Field of Search ................. 424/330; 260/570.7 R

[56] References Cited

U.S. PATENT DOCUMENTS 3,205,136  9/1965  Tedeschi .............................. 424/330
3,221,054  11/1965  Arnold et al. ....................... 424/330
3,221,054  11/1965  Arnold ................................ 260/570.7
3,954,872  5/1976  Koppe et al. ................... 260/570.7 R

FOREIGN PATENT DOCUMENTS 687,189  2/1953  United Kingdom.
1,205,958  9/1970  United Kingdom.

*Primary Examiner*—Stanley J. Friedman
*Attorney, Agent, or Firm*—Hammond & Littell

[57] ABSTRACT

Pharmaceutical dosage unit compositions containing as an active ingredient racemic or optically active 1-(2',6'-dimethyl-phenoxy)-2-methylamino-propane of the formula

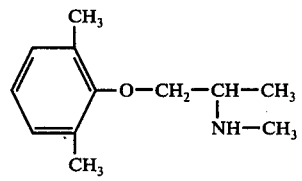

or a non-toxic, pharmaceutically acceptable acid addition salt thereof; and a method of using the same as anticonvulsives and antiarrhythmics.

2 Claims, No Drawings

PHARMACEUTICAL COMPOSITIONS CONTAINING RACEMIC OR OPTICALLY ACTIVE 1-(2,6-DIMETHYL-PHENOXY)-2-METHYLAMINO-PROPANE AND METHOD OF USE

This invention relates to novel pharmaceutical compositions containing racemic or optically active 1-(2',6'-dimethyl-phenoxy)-2-methylamino-propane or a non-toxic acid addition salt thereof, as well as to a method of using the same as anticonvulsives and antiarrhythmics.

More particularly, the present invention relates to novel pharmaceutical compositions containing as an active ingredient racemic or optically active 1-(2',6'-dimethyl-phenoxy)-2-methylamino-propane of the formula

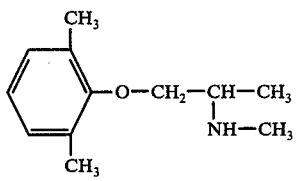

or a non-toxic, pharmaceutically acceptable acid addition salt thereof.

The racemic free base 1-(2',6'-dimethyl-phenoxy)-2-methylamino-propane is disclosed in U.S. Pat. No. 3,221,054 to Arnold et al, as is its preparation from 2,6-dimethyl-phenoxy-acetone and methylamine by reductive amination. The utility ascribed to the racemic free base in the prior art is its use as an intermediate in the preparation of the corresponding N-propargyl-substituted analog.

We have discovered that racemic and optically active 1-(2',6'-dimethyl-phenoxy)-2-methylamino-propane and non-toxic, pharmaceutically acceptable acid addition salts thereof have useful pharmacodynamic properties.

More particularly, we have discovered that these particular compounds exhibit a surprisingly strong anticonvulsive activity in warm-blooded animals, such as mice and that, unlike in other strong anticonvulsives, such as phenobarbital or diphenylhydantoin, the usual concurrent sedative activity is substantially absent.

We have further discovered that the active ingredients of the compositions according to the present invention also exhibit therapeutically useful antiarrhythmic activities in warm-blooded animals, such as mice, and that, unlike known antiarrhythmic pharmaceuticals, such as lidocaine, they can be perorally administered.

Thus, the compositions of the instant invention, containing racemic or optically active 1-(2',6'-dimethyl-phenoxy)-2-methylamino-propane or a non-toxic acid addition salt thereof as an active ingredient, are useful for the treatment of epilepsy and similar diseases, as well as cardiac arrhythmia.

The racemic free base disclosed in U.S. Pat. No. 3,221,054 can readily be separated into its optical antipode components by reaction with an optically active auxiliary acid, such as D-3-bromo-camphor-8-sulfonic acid or D-dibenzoyl-tartaric acid, followed by fractional crystallisation of the resulting diastereoisomeric salt.

The racemic or optically active free base forms acid addition salts with inorganic or organic acids. Examples of non-toxic, pharmaceutically acceptable acid addition salts are those formed with hydrochloric acid, hydrobromic acid, sulfuric acid, maleic acid, acetic acid, oxalic acid, lactic acid, tartaric acid, succinic acid, methanesulfonic acid, 8-chlorotheophylline or the like. These acid addition salts are prepared by conventional methods, that is, by neutralizing a solution of the free base with the desired acid or by double decomposition with a corresponding silver salt, such as silver methanesulfonate.

For pharmaceutical purposes in accordance with the present invention, racemic or optically active 1-(2',6'-dimethyl-phenoxy)-2-methylamino-propane or a non-toxic acid addition salt thereof is administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like.

The single effective anticonvulsive dosage range for oral administration is 0.16 to 2 mgm/kg body weight, preferably 0.33 to 1.3 mgm/kg. For parenteral administration the single effective anticonvulsive dosage range is 0.0016 to 0.33 mgm/kg body weight.

For the treatment of cardiac arrhythmia the compounds in question are, as a rule, initially administered intravenously at a dosage level of 1.6 to 5 mgm/kg body weight, which may be followed by intravenous drip administration at the rate of about 0.0016 to 0.05 mgm/kg per minute, i.e. up to 3 mgm/kg per hour, while monitoring the heart beat by means of an oscilloscope or electrocardiogram. Subsequently, if necessary, a sustaining dose of 1.6 to 3.3 mgm/kg p.o. three to four times daily is administered for as long as required.

In addition to racemic or optically active 1-(2',6'-dimethyl-phenoxy)-2-methylamino-propane or a non-toxic acid addition salt thereof, the pharmaceutical compositions of the present invention may contain one or more other active ingredients having different albeit complimentary pharmacodynamic properties. For example, compositions intended for use as anticonvulsives may also contain a tranquilizer of the benzodiazepine or phenothiazine type, or a spasmolytic of the scopolamine type; and compositions intended for use as antiarrhythmics may also contain a digitalis glycoside or a β-adrenergic receptor blocking agent.

The following examples illustrate the present invention and will enable others skilled in the art to understand it more completely. It should be understood, however, that the invention is not limited solely to the particular examples given below. The parts are parts by weight, unless otherwise specified.

EXAMPLE 1

Tablets

The tablet composition is compounded from the following ingredients:

| | |
|---|---|
| 1-(2',6'-Dimethyl-phenoxy)-2-methylamino-propane hydrochloride | 75.0 parts |
| Lactose | 25.0 parts |
| Secondary calcium phosphate | 150.0 parts |
| Corn starch | 206.0 parts |
| Colloidal silicic acid | 12.0 parts |
| Stearic acid | 4.0 parts |
| Soluble starch | 8.0 parts |
| Total | 480.0 parts |

Preparation:

The phenoxypropane salt is admixed with a major portion of the excipients, the mixture is moistened with an aqueous solution of the soluble starch, the moist mass is granulated in conventional manner through a screen, and the granulate is dried. The dry granulate is admixed with the remaining excipients, especially the stearic acid, and the resulting composition is compressed into 480 mgm-tablets in a conventional tablet making machine. Each tablet contains 75 mgm of the phenoxypropane salt and is an oral dosage unit composition with effective anticonvulsive and antiarrhythmic action.

EXAMPLE 2

Coated pills

The pill core composition is compounded from the following ingredients:

| | |
|---|---|
| 1-(2',6'-Dimethyl-phenoxy)-2-methylamino-propane methanesulfonate | 45.0 parts |
| Secondary calcium phosphate | 150 parts |
| Corn starch | 91.0 parts |
| Colloidal silicic acid | 7.0 parts |
| Magnesium stearate | 4.0 parts |
| Polyvinylpyrrolidone | 3.0 parts |
| Total | 300.0 parts |

Preparation:

The ingredients are compounded and granulated as described in Example 1, and the resulting composition is compressed into 300 mgm-pill cores which are subsequently coated in conventional manner with a thin shell consisting essentially of a mixture of sugar, titanium dioxide, talcum, gum arabic and polyvinylpyrrolidone. Each coated pill contains 45 mgm of the phenoxypropane salt and is an oral dosage unit composition with effective anticonvulsive and antiarrhythmic action.

EXAMPLE 3

Gelatin capsules

The capsule filler composition is compounded from the following ingredients:

| | |
|---|---|
| 1-(2',6'-Dimethyl-phenoxy)-2-methylamino-propane maleate | 50.0 parts |
| Lactose | 150.0 parts |
| Total | 200.0 parts |

Preparation:

The ingredients are intimately admixed with each other, and 200 mgm-portions of the mixture are filled into hard gelatin capsules of suitable size. Each capsule contains 50 mgm of the phenoxypropane salt and is an oral dosage unit composition with effective anticonvulsive and antiarrythmic action.

EXAMPLE 4

Hypodermic solution

The solution is compounded from the following ingredients:

| | |
|---|---|
| 1-(2',6'-Dimethyl-phenoxy)-2-methylamino-propane hydrochloride | 2.5 parts |
| Sodium salt of EDTA | 0.2 parts |
| Distilled water    q.s.ad | 100,000 parts by vol. |

Preparation:

The phenoxypropane salt and the EDTA salt are dissolved in the distilled water, the solution is filtered until free from suspended matter, and the filtrate is filled into 2 cc-ampules under aseptic conditions; the filled ampules are then sterilized and sealed. Each ampule contains 0.05 mgm of the phenoxypropane salt and its contents are an injectable solution with effective anticonvulsive and antiarrhythmic action.

EXAMPLE 5

Tablets with combination of active ingredients

The tablet composition is compounded from the following ingredients:

| | |
|---|---|
| 1-(2',6'-Dimethyl-phenoxy)-2-methylamino-propane hydrochloride | 60.0 parts |
| 5-Phenyl-7-chloro-1,3-dihydro-3-hydroxy-2H-1,4-benzodiazepin-2-one | 30.0 parts |
| Calcium phosphate | 150.0 parts |
| Starch | 206.0 parts |
| Colloidal silicic acid | 12.0 parts |
| Magnesium stearate | 4.0 parts |
| Soluble starch | 8.0 parts |
| Total | 470.0 parts |

Preparation:

The ingredients, except the soluble starch, are intimately admixed with each other, the mixture is moistened with an aqueous solution of the soluble starch, the moist mass is granulated by passing it through a screen, the granulate is dried, and the dry granulate is compressed into 470 mgm-tablets in a conventional tablet making machine. Each tablet contains 60 mgm of the phenoxy-propane salt and 30 mgm of the benzodiazepinone compound and is an oral dosage unit composition with effective anticonvulsive and tranquilizing action. The amount of active ingredient in these illustrative examples may be varied to achieve the dosage unit range set forth above, and the amounts and nature of the inert pharmaceutical carrier ingredients may be varied to meet particular requirements.

We claim:

1. An anticonvulsive or antiarrhythmic pharmaceutical dosage unit composition consisting essentially of an inert pharmaceutical carrier and an effective anticonvulsive or antiarrhythmic amount of racemic or optically active 1-(2',6'-dimethyl-phenoxy)-2-methylamino-propane or a non-toxic, pharmaceutically acceptable acid addition salt thereof.

2. The method of supressing convulsions or alleviating cardiac arrhythmia in a warm-blooded animal, which comprises perorally or parenterally administering to said animal an effective anticonvulsive or antiarrhythmic amount of racemic or optically active 1-(2',6'-dimethyl-phenoxy)-2-methylamino-propane or a non-toxic, pharmaceutically acceptable acid addition salt thereof.

* * * * *